United States Patent [19]

Munro et al.

[11] Patent Number: 5,304,532
[45] Date of Patent: Apr. 19, 1994

[54] HERBICIDAL COMPOUNDS

[75] Inventors: David Munro, Maidstone; Bipin Patel, Sittingbourne, both of England

[73] Assignee: Shell Research Limited

[21] Appl. No.: 707,026

[22] Filed: May 29, 1991

[30] Foreign Application Priority Data

Jul. 17, 1990 [GB] United Kingdom ............... 9015658

[51] Int. Cl.$^5$ ............... C07C 235/64; C07C 235/60; C07C 323/22; C07D 213/643
[52] U.S. Cl. ............................. 504/337; 564/162; 564/163; 564/174; 546/291; 546/301; 546/302; 546/300
[58] Field of Search ............... 546/291; 564/180, 162, 564/163, 174; 504/337

[56] References Cited

U.S. PATENT DOCUMENTS

| | | | |
|---|---|---|---|
| 3,012,872 | 12/1961 | Richter | 546/291 |
| 3,340,042 | 9/1967 | Schwartz et al. | 546/291 |
| 3,539,639 | 11/1970 | Mrozik | 546/291 |
| 3,719,707 | 3/1973 | Mrozik | 546/291 |
| 4,208,205 | 6/1980 | Fawzi | 546/291 |
| 4,602,943 | 7/1986 | Yamani et al. | 546/291 |

FOREIGN PATENT DOCUMENTS 2126149 12/1972 Fed. Rep. of Germany ...... 546/291

*Primary Examiner*—José G. Dees
*Assistant Examiner*—Keith MacMillan

[57] ABSTRACT

Compounds of the formula

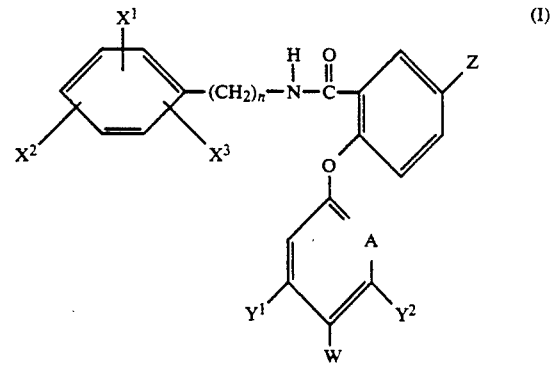

wherein $X^1$, $X^2$ and $X^3$ each independently represents hydrogen, halogen or alkyl; n is 0 or 1; Z represents hydrogen or halogen or an amino, alkyl, haloalkyl, alkylthio or alkoxy group or a phenoxy group optionally substituted by haloalkyl; A represents CH or N; $Y^1$ and Z$Y^2$ each independently represents hydrogen, halogen, alkyl, haloalkyl, alkoxy or haloalkoxy; and W represents hydrogen or, when A is CH and at least one of $Y^1$ and $Y^2$ is not hydrogen or when A is N, hydrogen or halogen; with the proviso that when A represents N, then each of $Y^1$ and $Y^2$ represents hydrogen, have herbicidal properties. The invention also provides a process for their preparation and their use as herbicides.

8 Claims, No Drawings

HERBICIDAL COMPOUNDS

The present invention concerns certain substituted benzanilides and related benzylamides, their preparation, herbicidal compositions containing them, and their use in combating undesired plant growth.

U.S. Pat. No. 3,719,707 discloses compounds of the general formula

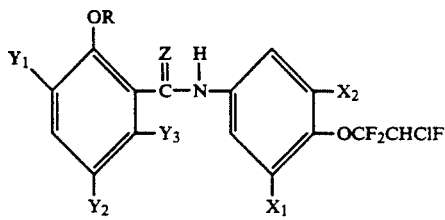

in which $X_1$ is halogen and $X_2$ is hydrogen or halogen; $Y_1$ and $Y_2$ are halogen; $Y_3$ is hydrogen or hydroxyl, Z is oxygen or sulphur, and R is hydrogen or lower alkanoyl, as bacteriocides and anthelmintic agents.

V. B. Angadi et al. in J. Karnatak Univ., 3, 63-64 (1958), reported in Chemical Abstracts 54, 3404i, discloses as useful in photographic materials, the compound

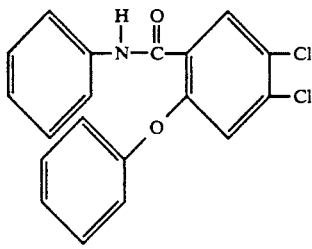

Other related compounds have also found use in photographic materials.

It has now been found that certain substituted benzanilides and benzylamides have useful herbicidal activity.

According to the present invention, there is provided a compound of the general formula

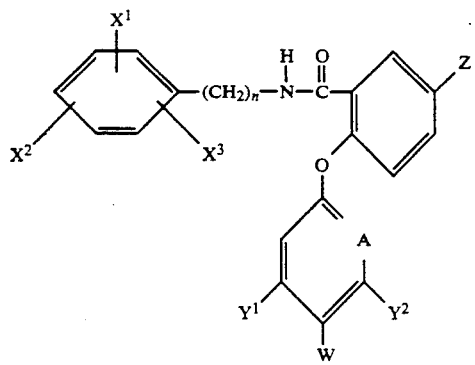

(I)

wherein $X^1$, $X^2$ and $X^3$ each independently represents a hydrogen or halogen atom or an alkyl group; n is 0 or 1; Z represents a hydrogen or halogen atom, or an amino, alkyl, haloalkyl, alkylthio or alkoxy group or a phenoxy group optionally substituted by haloalkyl; A represents CH or N; $Y^1$ and $ZY^2$ each independently represents a hydrogen or halogen atom, or an alkyl, haloalkyl, alkoxy or haloalkoxy group; and either W represents hydrogen atom or, when A represents CH and at least one of $Y^1$ and $Y^2$ is other than hydrogen or when A represents N, W represents a hydrogen or halogen atom; with the proviso that when A represents N, then each of $Y^1$ and $Y^2$ must represent a hydrogen atom.

An alkyl substituent group or alkyl moiety in a haloalkyl, alkylthio, alkoxy or haloalkoxy substituent group, may be linear or branched and preferably has up to 12, preferably up to 6 and especially up to 4, carbon atoms. A preferred alkyl group or moiety is methyl. A preferred haloalkyl group or moiety is trifluoromethyl.

Preferably each of $X^1$, $X^2$ and $X^3$ independently represents a hydrogen or halogen atom or a $C_1$-$C_4$ alkyl group. More preferably $X^1$, $X^2$ and $X^3$ each independently represents a hydrogen, fluorine or chlorine atom or a methyl group. In especially preferred compounds one or more of $X^1$, $X^2$ and $X^3$ represents a hydrogen, fluorine or chlorine atom.

Z preferably represents a hydrogen or halogen atom, or an amino, $C_1$-$C_4$ alkyl, $C_1$-$C_4$ haloalkyl, $C_1$-$C_4$ alkylthio, suitably methylthio, or $C_1$-$C_4$ alkoxy group or a phenoxy group optionally substituted by $C_1$-$C_4$ haloalkyl. More preferably, Z represents a hydrogen, fluorine, chlorine or bromine atom, or a methyl, trifluoromethyl, methoxy or 3-trifluoromethylphenoxy group. In especially preferred compounds, Z represents a hydrogen, fluorine or chlorine atom or a methyl group.

Preferably each of $Y^1$ and $Y^2$ independently represents a hydrogen or halogen atom, or a $C_1$-$C_4$ alkyl, $C_1$-$C_4$ haloalkyl, $C_1$-$C_4$ alkoxy or $C_1$-$C_4$ haloalkoxy group. More preferably, one of $Y^1$ and $Y^2$ represents a hydrogen, fluorine or chlorine atom, or a methyl, trifluoromethyl, methoxy or trifluoromethoxy group, and the other represents a hydrogen atom. In especially preferred compounds one of $Y^1$ and $Y^2$ represents a hydrogen or chlorine atom or a trifluoromethyl or trifluoromethoxy group, and the other represents a hydrogen atom.

A represents CH or N. When A represents N, then each of $Y^1$ and $Y^2$ must represent a hydrogen atom to maintain herbicidal activity. In preferred compounds, however, A represents a CH group.

W suitably represents a hydrogen atom or, in certain compounds, i.e. those in which A is CH and at least one of $Y^1$ and $Y^2$ is other than hydrogen and especially those compounds in which A is N, W may alternatively represent a halogen atom, conveniently a fluorine or chlorine atom. In especially preferred compounds, W represents a hydrogen atom.

The present invention also provides a process for the preparation of a compound of formula I as defined above which comprises reacting, where necessary in the presence of a suitable base, a compound of the general formula

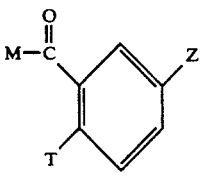

(II)

in which M represents a leaving group and T represents a group of the general formula

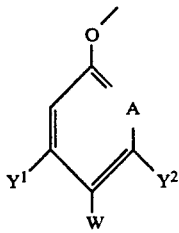

(III)

or M represents a group of the general formula

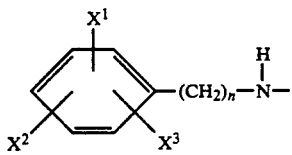

(IV)

and T represents a leaving group, with a compound of the general formula

Q-L   (V)

in which, when M represents a leaving group and T represents a group III then Q represents the group

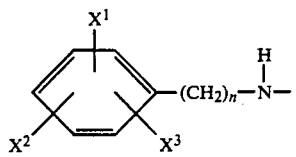

and L represents a hydrogen atom, or, when M represents a group IV and T represents a leaving group, then Q represents the group

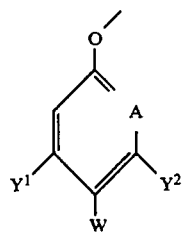

and L represents a hydrogen atom or univalent cation, and $X^1$, $X^2$, $X^3$, n, Z, A, $Y^1$, $Y^2$ and N are as defined above.

A leaving group is any group that will, under the reaction conditions, cleave from the starting material thus promoting reaction at a specific site.

When present as a leaving group in a compound of formula II, M is conveniently a halogen atom, preferably a chlorine atom, when A in the group T is CH. When A in the group T is N, then M is suitably a hydroxy group.

When present as a leaving group in a compound of formula II, T is conveniently a halogen atom, suitably a fluorine or chlorine atom.

The reaction of a compound of formula II in which M represents a leaving group and T represents a group III with a phenyl- or benzyl-amine of formula V, is suitably carried out using conventional techniques for such reactions.

The presence of a base is required for this process variant; suitable bases include organic bases, for example tertiary amines, e.g. triethylamine and N-methylmorpholine.

The reaction of a compound of formula II in which M represents a group IV and T represents a leaving group, with a phenol or pyridinol of formula V or a reactive salt derivative thereof, i.e. where L is a cation, is especially suitable where Z is a strongly electron-withdrawing group, for example a trifluoromethyl group. Following the reaction, the resulting compound of the invention may be converted to other compounds of the invention, for example to those in which Z is amino, by conventional techniques, e.g. reduction.

In this reaction variant a base is required when the compound V is a phenol or pyridinol, to generate the reactive salt derivative, especially an alkali metal salt, of the phenol or pyridinol V in situ. Suitable bases include alkali metal hydrides, e.g. sodium or potassium hydride, alkali metal alkoxides, e.g. sodium ethoxide, or alkali metal hydroxides, e.g. sodium or potassium hydroxide.

If, however, the phenol or pyridinol is already in the form of a reactive salt derivative, i.e. if L is a cation, then it is no longer necessary to carry out the reaction in the presence of a base.

Both variants of the process of the invention are conveniently carried out in the presence of an organic solvent. Suitable solvents include polar organic solvents, e.g. dimethylformamide dimethylsulphoxide and tetrahydrofuran, and hydrocarbon solvents, e.g. toluene.

The reaction temperature for each process variant will be determined by the reaction materials used and the coupling technique selected. Generally, process of the present invention may be carried out at a temperature in the range of from $-30°$ C. to the reflux temperature of the reaction mixture. Where compounds of formula I are prepared in which A is CH, the reaction is conveniently carried out at a temperature in the range of from ambient (20° C.) to the reflux temperature. For compounds in which A is N, the reaction is suitably carried out at a temperature in the range of from $-20°$ C. to 0° C., for example at $-15°$ C.

Preferably the molar ratio of compound V to compound II is in the range of from 1:1 to 1.2:1.

Where A is N, it is preferred to use the synthesis route in which an aryl phenyl ether II is reacted with a phenyl- or benzyl-amine V utilising a peptide coupling agent, for example isobutylchloroformate or dicyclohexylcarbodiimide.

The compounds of the present invention may be isolated and purified by conventional techniques.

Compounds of formula II in which M represents a leaving group and T represents a group III may be conveniently prepared by hydrolysing a compound of the general formula

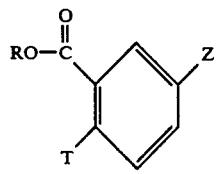

(VI)

in which Z is as defined above and R represents an alkyl, preferably $C_1$–$C_6$ alkyl, group, to the corresponding carboxylic acid, in the presence of a base such as potassium hydroxide, or by hydrolysing a compound of the general formula

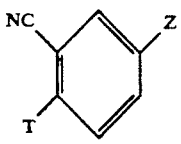
(VII)

in which Z is as defined above, to the corresponding carboxylic acid, in the presence of a base such as potassium hydroxide, optionally followed in each case by reaction with a halogenating agent such as thionyl chloride, to form an acid halide of formula II, i.e. in which M is a halogen atom.

Compounds of the formula VI may be prepared by reacting a compound of the general formula

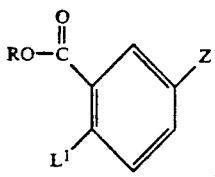
(VIII)

in which R and Z are as defined above and $L^1$ represents a leaving group, preferably a halogen, suitably a chlorine or bromine, atom, with a compound of the general formula

T-H   (IX)

in which T is a group III, under Ullmann coupling conditions, for example using the sodium salt of compound IX in the presence of a copper (I) salt, e.g. cuprous chloride, and as co-solvents xylene and pyridine. This synthesis route is only suitable for compounds in which Z is other than halogen, and is, for example, an electron-donating group e.g. methoxy or methylthio.

Alternatively compounds of formula VI in which A is N may be prepared by reacting a compound of the general formula

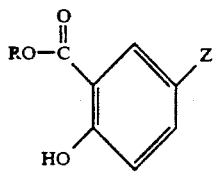
(X)

in which $R^1$ and Z are as defined above, with a compound of the general formula $T^1$-$L^2$   (XI)

in which $L^2$ represents a leaving group, preferably a halogen, especially a chlorine, atom and $T^1$ represents a group of the general formula

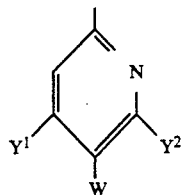
(XII)

in which $Y^1$, $Y^2$ and W are as defined above, in the presence of a strong base such as sodium hydride, with a polar organic solvent such as dimethylformamide.

Compounds of the formula VII may be prepared by reacting a compound of the general formula

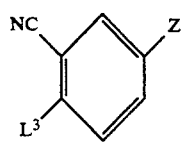
(XIII)

in which Z is as defined above and $L^3$ represents a leaving group, preferably a halogen, especially a fluorine or chlorine, atom, with a compound of formula IX as defined above, in the presence of a base such as potassium hydroxide, using a polar organic solvent such as dimethylformamide.

Compounds of the formula V, VIII, IX, X, XI and XIII are either known compounds or can be prepared using conventional techniques.

Compounds of formula II in which M represents a group IV and T represents a leaving group may be conveniently prepared by reacting a compound of the general formula

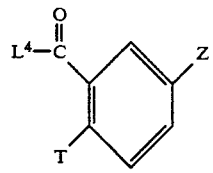
(XIV)

in which Z and T are as defined above and $L^4$ represents a leaving group preferably a halogen, especially a chlorine, atom, with a compound of the general formula

M-H   (XV)

in which M is as defined above, in the presence of a base such as triethylamine, and an organic solvent such as xylene or toluene.

Compounds of the formula XIV may be prepared by reacting a compound of the general formula

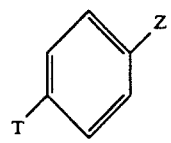
(XVI)

in which Z is as defined above and T is a leaving group with a strong base such as an organolithium, e.g. butyl lithium, followed by aqueous work-up, followed there-after by reaction with a halogenating agent such as thionyl chloride, in an organic solvent, e.g. toluene or xylene, under nitrogen.

Compounds of the formulae XV and XVI are either known compounds or can be prepared by conventional techniques.

The compounds of general formula I have been found to have useful herbicidal activity. Accordingly, the present invention further provides a herbicidal composition which comprises a carrier and, as active ingredient, a compound of formula I as defined above. A method of making such a composition is also provided which comprises bringing a compound of formula I as defined above into association with at least one carrier.

A composition according to the present invention preferably contains in the range of from 0.5% to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing $\frac{1}{2}$–10% w of active ingredient. Granules are usually prepared to have a size between 10 and 100 BS mesh (1.676–0.152 mm), and may be manufactured by agglomeration or impregnation techniques. Generally, granules will contain $\frac{1}{2}$–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other active ingredients, for example compounds possessing insecticidal or fungicidal properties or other herbicides.

The present invention still further provides the use as a herbicide of a compound of the general formula I as defined above or a composition as defined above and a method of combating undesired plant growth at a locus with such a compound or composition. The locus may be, for example, the soil or plants in a crop area. The dosage of active ingredient may, for example, be in the

Example 1

Preparation of 2-(3-trifluoromethylphenoxy)-5-fluorobenzoic acid-2',4'-difluoroanilide ($X^1$=2—F; $X^2$=4—F; $X^3$=H; n=0; Z=F; A=CH; $Y^1$=CF$_3$; $Y^2$=H; W=H)

(i) Preparation of 2-(3-trifluoromethylphenoxy)-5-fluorobenzonitrile

To a solution of 3-trifluoromethylphenol (29 g, 0.18 mol) dissolved in dimethylformamide (100 ml) was added finely-powdered potassium hydroxide (15 g, 0.19 mol). The reaction mixture was heated to approximately 60° C., with stirring, for one hour after which time 2,5-difluorobenzonitrile (25 g, 0.19 mol) was added and the temperature increased to 110° C. After approximately half an hour, the reaction mixture was allowed to cool and excess dimethylformamide was removed in vacuo before 500 ml of a 50:50 mixture of water and trichloromethane was added. The organic layer was separated, washed and dried and the residue purified by chromatography using a silica column with trichloromethane as eluant, followed by distillation and recrystallisation to yield the title compound as a solid.

Melting point: 51° C.
Analysis (%) Calc. C: 59.8; H: 2.5; N: 5.0
Found C: 59.8; H: 2.7; N: 5.2

(ii) Preparation of 2-(3-trifluoromethylphenoxy)5-benzoic acid 2-(3-Trifluoromethylphenoxy)-5-fluorobenzonitrile obtained in (i) above (12 g, 0.04 mol) was added to ethylene glycol (15 ml) and to this solution was added potassium hydroxide (10 g, 0.125 mol) dissolved in water (10 ml). The reaction mixture was refluxed for approximately four hours, cooled, and water (150 ml) added. The mixture was then extracted with diethyl ether (100 ml) and the aqueous layer acidified before further extraction with trichloromethane (3×150 ml). The organic layer was separated, washed, dried and chromatographed on a silica column using 3:2 (v/v) trichloromethane : ethyl acetate as eluant to give the title compound as a colourless solid (10 g, mol, 74% yield).

Melting point: 106° C.
Analysis (%) Calc. C: 56.0; H: 2.7
Found C: 55.9; H: 2.7

(iii) Preparation of 2-(3-trifluoromethylphenoxy)-5-fluorobenzoic acid-2',4'-difluoroanilide To a solution of 2-(3-trifluoromethylphenoxy)-5-benzoic acid obtained in (ii) above (6 g, 0.02 mol) in toluene (60 ml) was added thionyl chloride (6 ml). The reaction mixture was refluxed for one hour and solvent subsequently removed to leave a residue. The residue was then redissolved in toluene (25 ml) and the resulting solution added to a mixture of 2,4-difluoroaniline (2.6 g, 0.02 mol) and triethylamine (3 g, 0.03 mol) in toluene (25 ml) and the reaction allowed to proceed at ambient temperature ~20° C.). Once all reaction had ended, the reaction mixture was filtered and the filtrate chromatographed on a silica column using trichloromethane as eluant to give 2-(3-trifluoromethylphenoxy)-5-fluorobenzoic acid-2',4'-difluoroanilide as a colourless solid (6.2 g, 0.015 mol, 76% yield).

Melting point: 98° C.
Analysis (%) Calc. C: 58.4; H: 2.7; N: 3.4
Found C: 58.9; H: 2.8; N: 3.7

Example 2

Preparation of 2-(3-trifluoromethylphenoxy)-5-trifluoromethyl-benzoic acid-2',4'-difluoroanilide ($X^1$=2—F; $X^2$=4—F; $X^3$=H; n=0; Z=CF$_3$; A=CH; $Y^1$=CF$_3$; $Y^2$=H; W=H)

(i) Preparation of 3-carboxy,4-fluorobenzotrifluoride

To a solution of 4-fluorobenzotrifluoride (75 ml) in tetrahydrofuran (570 ml) under a nitrogen atmosphere and at a temperature of approximately −60° C. was added butyl lithium (25N, 200 ml) over a period of one hour. The reaction mixture was stirred at from −70° to −60° C. for four hours and then was poured over an excess of dry ice. After fifteen minutes the excess dry ice was evaporated and the solvent removed to leave a residue. The residue was taken up in water (500 ml) and sodium hydroxide (1N, 30 ml) prior to washing with ethyl acetate (2×300 ml). The aqueous phase was acidified with concentrated hydrochloric acid and extracted with ethyl acetate (2x300 ml). Finally, the combined organic extracts were washed with water (500 ml), dried and then evaporated to yield a crude residue which, upon recrystallisation from toluene/hexane, gave the title compound as a solid (77 g, 0.37 mol, 81% yield).

Melting point: 100° C.
Analysis (%) Calc. C: 46.2; H: 1.9
Found C: 46.1; H: 1.7

(ii) Preparation of 2-fluoro-5-trifluoromethylbenzoic acid-2',4'-difluoroanilide 3-Carboxy,4-fluorobenzotrifluoride obtained in (i) above (10 g, 0.05 mol) was dissolved in toluene (100 ml) and excess thionyl chloride (10 ml) added dropwise whilst stirring under a nitrogen atmosphere. After one hour, the solvent was removed to leave a residue which was subsequently redissolved in toluene (50 ml) and added to a mixture of 2,4-difluoroaniline (6.2 g, 0.05 mol) and triethylamine (7 g, 0.07 mol) in toluene (50 ml). The reaction mixture was filtered to obtain a precipitate-free filtrate from which solvent was subsequently removed to yield a residue. Purification of the residue on a silica column using trichloromethane as eluant gave the title compound as a colourless solid (10.6 g, 0.03 mol, 69% yield).

Melting point: 126° C.
Analysis (%) Calc. C: 52.7; H: 2.2; N: 4.4
Found C: 53.3; H: 2.2; N: 4.7

(iii) Preparation of 2-(3-trifluoromethylphenoxy)-5-trifluoromethylbenzoic acid-2',4'-difluoroanilide To a suspension of oil-free sodium hydride (0.7 g, 0.03 mol) in dry tetrahydrofuran (50 ml) was added 3-trifluoromethylphenol (3.6 g, 0.022 mol) in small portions and 2-fluoro-5-trifluoromethylbenzoic acid-2',4'-difluoroanilide obtained in (ii) above (7 g, 0.022 mol) in a single portion. Reflux of the reaction mixture for one hour was followed by removal of solvent and partitioning of the remaining residue between trichloromethane and water (500 ml, 50:50 v/v). The organic layer was separated, washed, then dried and finally purified on a silica column using trichloromethane as eluant to give the title compound as a colourless solid (6.8 g, 0.015 mol, 67% yield).

Melting point: 105° C.
Analysis (%) Calc. C: 54.7; H: 2.4; N: 3.0
Found C: 55.6; H: 2.6; N: 3.0

Example 3

Preparation of 2-(3-trifluoromethylphenoxy)-5-methoxybenzoic acid-2',4'-difluoroanilide ($X^1$=2—F; $X^2$=4—F; $X^3$=H; n=0; Z=OCH$_3$; A=CH; $Y^1$=CF$_3$; $Y^2$=H; W=H)

(i) Preparation of methyl-2-(3-trifluoromethylphenoxy)-5-methoxy benzoate

Sodium (5.4 g, 0.23 mol) in methanol (90 ml) was added to a solution of 3-trifluoromethylphenol (36 g, 0.22 mol) in xylene (200 ml) and the xylene then removed. Fresh xylene (200 ml) was added and subsequently evaporated in vacuo. Further fresh xylene (200 ml) was added followed by cuprous chloride (6 g, 0.06 mol) and pyridine (100 ml). 2-Bromo-5-methoxy benzoic acid methyl ester (50 g, 0.20 mol) in xylene (50 ml) was then added and the resulting mixture refluxed overnight before pouring into water (1000 ml), acidifying with dilute hydrochloric acid and extracting with diethyl ether (2×500 ml). The organic layer was separated and chromatographed on a silica column using a 50:50 (v/v) mixture of trichloromethane and hexane as eluant to give the title compound as a colourless oil (55.2 g, 0.17 mol, 83% yield).

Boiling point: 140° C. at approximately 1 mmHg.
Analysis (%) Calc. C: 58.9; H: 4.0
Found C: 58.6; H: 4.1

(ii) Preparation of 2-(3-trifluoromethylphenoxy)-5-methoxybenzoic acid

Methyl-2-(3-trifluoromethylphenoxy)-5-methoxybenzoate obtained in (i) above (10 g; 0.03 mol) was dissolved in methanol (20 ml) and 10% aqueous solution potassium hydroxide (50 ml) added. The reaction mixture was refluxed until homogeneous (30 minutes), acidified with 2N hydrochloric acid, and water added (300 ml) The resulting mixture was extracted with trichloromethane (2×150 ml) and the combined extracts chromatographed on a silica column using a 80:20 (v/v) mixture of trichloromethane and ethyl acetate as eluant to give a colourless solid. Recrystallisation of the solid from toluene/hexane gave the title compound as colourless crystals (7.5 g, 0.024 mol, 78% yield). Melting point: 124° C.

Analysis (%) Calc. C: 57.7; H: 3.5
Found C: 57.6; H: 3.9

(iii) Preparation of 2-(3-trifluoromethylphenoxy)-5-methoxybenzoic acid-2',4'-difluoroanilide To a solution of 2-(3-trifluoromethylphenoxy)-5-methoxybenzoic acid obtained in (ii) above (6 g; 0.02 mol) in toluene (60 ml) was added thionyl chloride (6 ml). The reaction mixture was refluxed for one hour and the solvent subsequently removed to leave a residue. The residue was then redissolved in toluene (25 ml) and the resulting solution added to a mixture of 2,4-difluoroaniline (2.6 g, 0.02 mol) and triethylamine (3 g; 0.03 mol), and the reaction allowed to proceed at ambient temperature (approximately 20° C.). Once all reaction had ended, the reaction mixture was filtered and the filtrate chromatographed on a silica column using trichloromethane as eluant to give a colourless solid. Recrystallisation of the solid from hexane/ethyl acetate yielded the title compound as colourless crystals (6.5 g, 0.015 mol, 80% yield). Melting point: 112° C.

Analysis (%) Calc. C: 59.6; H: 3.3; N: 3.3
Found C: 59.9; H: 3.5; N: 3.7

Example 4

Preparation of 2-(5-chloro-2-pyridyloxy)benzoic acid-2',4'-difluoroanilide ($X^1$=2—F; $X^2$=4—F; $X^3$=H; n=0; Z=H; A=N; $Y^1$=H; $Y^2$=H; W=Cl)

(i) Preparation of ethyl-2-(5-chloro-2-pyridyloxy)-benzoate

Ethyl salicylate (30 g, 0.18 mol) was added dropwise with stirring to a suspension of oil-free sodium hydride (5 g, 0.21 mol) in dry dimethylformamide (100 ml) under a nitrogen atmosphere. After one hour, 2,5-dichloropyridine (26 g, 0.17 mol) was added and the reaction mixture refluxed for 48 hours. The dimethylformamide was then removed in vacuo and 1 l of a 50:50 (v/v) mixture of water and trichloromethane added to the remaining residue. The organic layer was separated, washed, dried and, finally, chromatographed on a silica column using trichloromethane and hexane (3:1, v/v) as eluant to give the title compound as a colourless oil (32.1 g, 0.115 mol, 64% yield).

Boiling point: 150° C. at approximately 1 mmHg.
Analysis (%) Calc. C: 60.5; H: 4.3; N: 5.1
Found C: 60.5; H: 4.4; N: 5.1

(ii) Preparation of 2-(5 chloro-2-pyridyloxy)benzoic acid

To a solution of ethyl-2-(5-chloro-2-pyridyloxy)benzoate obtained in (i) above (30 g, 0.11 mol) dissolved in ethanol (50 ml) was added a 10% aqueous solution of potassium hydroxide (120 ml). The reaction mixture was refluxed with stirring for thirty minutes until it was homogeneous. The reaction mixture was then acidified (to pH 2-3) with aqueous hydrochloric acid and extracted with trichloromethane (500 ml). The organic layer was separated, dried and subsequently chromatographed on a silica column using a 50:50 v/v mixture of trichloromethane and ethyl acetate as eluant to give the title compound as a colourless solid (19.7 g, 0.08 mol, 73% yield).

Melting point: 159° C.
Analysis (%) Calc. C: 57.7; H: 3.2; N: 5.6
Found C: 57.7; H: 3.2: N: 5.7

(iii) Preparation of 2-(5-chloro-2-pyridyloxy)benzoic acid-2',4'-difluoroanilide 2-(5-chloro-2-pyridyloxy)benzoic acid obtained in (ii) above (1.5 g, 0.006 mol) was dissolved in dry tetrahydrofuran (20 ml), cooled to -15° C. and then treated sequentially with N-methylmorpholine (1 ml) and isobutylchloroformate (1 ml). The resulting mixture was stirred at approximately −15° C. for one minute before 2,4-difluoroaniline (0.8 g, 0.006 mol) was added. The mixture was stirred for a further thirty minutes at the same temperature after which time a 10% v/v aqueous solution of citric acid (50 ml) was added. Extraction with ethyl acetate (3×50 ml) followed; the organic extracts were combined, dried and then chromatographed on a silica column to give the title compound as a colourless solid (1.2 g, 0.0033 mol, 54% yield).

Melting point: 138° C.
Analysis (%) Calc. C: 59.9; H: 3.1; N: 7.8
Found C: 60.2; H: 3.1: N: 7.5

Examples 5 to 41

By processes analogous to those described in Examples 1 to 4 above, further compounds according to the invention were prepared as detailed in Table I below. In Table I, the compounds are identified by reference to formula I. Melting/boiling point data and elemental analysis data for the compounds of Examples 5 to 41 are given in Table IA below.

TABLE 1

| Example No. | $X^1$ | $X^2$ | $X^3$ | n | Z | A | $Y^1$ | $Y^2$ | W |
|---|---|---|---|---|---|---|---|---|---|
| 5 | H | H | H | 0 | H | CH | H | H | H |
| 6 | 2-F | 4-F | H | 0 | H | CH | H | H | H |
| 7 | H | H | H | 0 | H | CH | $CF_3$ | H | H |
| 8 | 2-F | 4-F | H | 0 | H | CH | $CF_3$ | H | H |
| 9 | 2-$CH_3$ | 4-$CH_3$ | H | 0 | F | CH | $CF_3$ | H | H |
| 10 | H | H | H | 0 | F | CH | $CF_3$ | H | H |
| 11 | 2-F | H | H | 0 | F | CH | $CF_3$ | H | H |
| 12 | 4-F | H | H | 0 | F | CH | $CF_3$ | H | H |
| 13 | 2-F | 5-F | H | 0 | F | CH | $CF_3$ | H | H |
| 14 | 2-F | 4-F | 5-F | 0 | F | CH | $CF_3$ | H | H |
| 15 | 2-F | 4-Cl | H | 0 | F | CH | $CF_3$ | H | H |
| 16 | 2-F | 4-F | H | 0 | F | CH | $CF_3$ | H | Cl |
| 17 | 2-F | 4-F | H | 0 | H | CH | $CH_3$ | $CH_3$ | H |
| 18 | 2-F | 4-F | H | 0 | H | CH | Cl | H | H |
| 19 | 2-F | 4-F | H | 0 | F | CH | Cl | H | H |
| 20 | 2-F | 4-F | H | 0 | F | CH | Cl | H | F |
| 21 | 2-F | 4-F | H | 0 | F | CH | F | H | H |
| 22 | 2-F | 4-F | H | 0 | F | CH | $OCH_3$ | H | H |
| 23 | 2-F | 4-F | H | 0 | F | CH | $OCF_3$ | H | H |
| 24 | H | H | H | 0 | F | CH | H | H | H |
| 25 | 2-F | 4-F | H | 0 | Cl | CH | $CF_3$ | H | H |
| 26 | 2-F | 4-F | H | 0 | $NH_2$ | CH | $CF_3$ | H | H |
| 27 | 2-F | 4-F | H | 0 | 3-trifluoromethyl-phenoxy | CH | $CF_3$ | H | H |
| 28 | H | H | H | 1 | H | CH | $CF_3$ | H | H |
| 29 | H | H | H | 1 | Cl | CH | $CF_3$ | H | H |
| 30 | H | H | H | 1 | F | CH | $CF_3$ | H | H |
| 31 | 2-$CH_3$ | H | H | 1 | F | CH | $CF_3$ | H | H |
| 32 | 3-F | 4-F | H | 0 | F | CH | $CF_3$ | H | H |
| 33 | 3-F | H | H | 0 | F | CH | $CF_3$ | H | H |
| 34 | 4-Cl | H | H | 0 | F | CH | $CF_3$ | H | H |
| 35 | 2-F | 4-F | 5-F | 0 | F | CH | $OCF_3$ | H | H |
| 36 | 4-F | H | H | 0 | F | CH | $OCF_3$ | H | H |
| 37 | 2-F | 4-F | H | 0 | $CH_3$ | CH | $CF_3$ | H | H |
| 38 | 2-F | 4-F | H | 0 | $SCH_3$ | CH | $OCF_3$ | H | H |
| 39 | 2-F | 4-F | H | 0 | $CH_3$ | CH | $OCF_3$ | H | H |
| 40 | 4-F | H | H | 0 | $CH_3$ | CH | $OCF_3$ | H | H |
| 41 | 2-F | 4-F | H | 0 | Br | CH | $CF_3$ | H | H |

TABLE IA

| Example No. | Melting point (°C.) | Analysis (%) | | | | | |
|---|---|---|---|---|---|---|---|
| | | C | | H | | N | |
| | | Calc. | Found | Calc. | Found | Calc. | Found |
| 5 | 98 | 78.9 | 78.9 | 5.2 | 5.2 | 4.8 | 5.0 |
| 6 | 89 | 70.2 | 70.5 | 4.0 | 4.0 | 4.3 | 4.3 |
| 7 | 74 | 67.2 | 66.8 | 3.9 | 3.9 | 3.9 | 4.4 |
| 8 | 99 | 61.1 | 61.1 | 3.0 | 3.0 | 3.6 | 3.6 |
| 9 | 112 | 65.5 | 64.9 | 4.2 | 4.6 | 3.5 | 4.1 |
| 10 | 126 | 64.0 | 63.9 | 3.5 | 3.5 | 3.7 | 4.0 |
| 11 | 119 | 61.1 | 60.9 | 3.0 | 3.3 | 3.6 | 3.9 |
| 12 | 119 | 61.1 | 61.2 | 3.0 | 3.2 | 3.6 | 3.6 |
| 13 | 142 | 58.4 | 58.0 | 2.7 | 3.3 | 3.4 | 3.6 |
| 14 | 114 | 55.9 | 56.1 | 2.3 | 2.6 | 3.3 | 3.6 |
| 15 | 105 | 56.1 | 56.5 | 2.6 | 2.8 | 3.3 | 4.0 |
| 16 | 128 | 53.9 | 53.7 | 2.2 | 2.3 | 3.1 | 3.4 |
| 17 | 94 | 71.4 | 71.6 | 4.8 | 4.9 | 4.0 | 4.0 |
| 18 | 101 | 63.4 | 63.5 | 3.3 | 3.5 | 3.9 | 4.3 |
| 19 | 87 | 60.4 | 60.6 | 2.9 | 3.0 | 3.7 | 3.7 |
| 20 | 134 | 57.7 | 57.8 | 2.5 | 2.8 | 3.5 | 3.7 |
| 21 | 104 | 63.2 | 63.2 | 3.0 | 3.2 | 3.9 | 3.9 |
| 22 | 112 | 64.3 | 64.3 | 3.8 | 3.8 | 3.8 | 3.9 |
| 23 | 95 | 56.2 | 56.7 | 2.6 | 2.8 | 3.3 | 3.9 |
| 24 | 117 | 74.3 | 74.0 | 4.6 | 4.7 | 4.6 | 5.0 |
| 25 | 114 | 56.1 | 56.0 | 2.6 | 2.6 | 3.3 | 3.5 |
| 26 | 128 | 58.8 | 58.4 | 3.2 | 3.2 | 6.9 | 7.1 |
| 27 | oil (boiling point: 200° C./1 mmHg) | 58.6 | 58.6 | 2.7 | 2.7 | 2.5 | 2.5 |
| 28 | oil (boiling point: 230° C./4 mmHg) | 67.9 | 67.9 | 4.3 | 4.3 | 3.8 | 4.1 |
| 29 | oil (boiling point: 190° C./1 mmHg) | 62.1 | 62.3 | 3.7 | 3.7 | 3.5 | 3.8 |
| 30 | 98 | 64.8 | 65.0 | 3.9 | 4.0 | 3.6 | 3.8 |
| 31 | 101 | 65.5 | 65.1 | 4.2 | 4.3 | 3.5 | 3.6 |
| 32 | 109 | 58.4 | 58.2 | 2.7 | 3.1 | 3.4 | 3.4 |
| 33 | 120 | 61.1 | 61.3 | 3.1 | 3.2 | 3.6 | 3.4 |
| 34 | 115 | 58.7 | 58.9 | 2.9 | 3.0 | 3.4 | 3.8 |
| 35 | 113 | 53.9 | 53.9 | 2.2 | 2.5 | 3.1 | 3.0 |
| 36 | 102 | 58.7 | 58.8 | 2.9 | 3.2 | 3.4 | 3.4 |
| 37 | 68 | 61.9 | 61.8 | 3.4 | 3.3 | 3.4 | 3.5 |
| 38 | 87 | 55.4 | 55.1 | 3.1 | 2.7 | 3.1 | 3.1 |
| 39 | 80 | 59.6 | 59.3 | 3.3 | 3.1 | 3.3 | 3.7 |
| 40 | 126 | 62.2 | 62.4 | 3.7 | 3.9 | 3.5 | 3.8 |
| 41 | 103 | 50.8 | 50.6 | 2.3 | 2.5 | 3.0 | 2.9 |

Example 42

Herbicidal Activity

To evaluate their herbicidal activity, compounds according to the invention were tested using as representative range of plants: maize, *Zea mays* (Mz); rice, *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant specied mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table II below, in which the compounds are identified by reference to the preceding Examples. Absence of a numeral in the Table indicates a zero rating; an asterisk indicates that no result was obtained.

TABLE II

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 1 | 4 | 1 | 4 | 4 | 2 | 2 | 4 | | 5 | 6 | 4 | 8 | 6 | 7 | 9 | 9 | 8 | 5 | 3 | 9 | 7 | 4 | 9 | 9 | 3 |
| | | | | | | | | | 1 | 4 | 3 | 7 | 5 | 6 | 9 | 9 | 8 | 3 | 2 | 9 | 6 | 2 | 8 | 8 | 2 |
| 2 | | | | | | 2 | 1 | | 5 | 1 | | 2 | 1 | 2 | 7 | 3 | 2 | | | | | | 2 | 2 | |
| | | | | | | | | | 1 | 1 | | 1 | | 2 | 7 | 3 | 2 | | | | | | | 2 | |
| 3 | | | | | | | | | 5 | 4 | | 3 | 1 | * | * | * | * | | | | | | 2 | 1 | |
| | | | | | | | | | 1 | 1 | | 2 | 1 | 4 | 8 | 4 | 4 | | | | | | 2 | | |
| 4 | | | | | | | | | 5 | 2 | | 5 | 1 | 4 | 8 | 5 | 4 | | | | | 2 | 5 | 2 | |
| | | | | | | | | | 1 | 1 | | 3 | | 3 | 8 | 4 | 4 | | | | | | 3 | | |
| 5 | | | 4 | | 2 | 2 | 2 | | 5 | 4 | | 5 | 3 | 5 | 9 | 9 | 4 | | | 1 | | | 3 | | |
| | | | | | | | | | 1 | 2 | | 4 | 1 | 4 | 9 | 9 | 3 | | | 1 | | | 2 | | |
| 6 | | | | | | | | | 5 | 4 | | 7 | 2 | 6 | 9 | 8 | 5 | | | | | | | | |
| | | | | | | | | | 1 | 2 | | 3 | 1 | 3 | 9 | 8 | 3 | | | | | | | | |
| 7 | | | 2 | | 1 | 2 | 3 | | 5 | 4 | 1 | 8 | 4 | 6 | 9 | 9 | 5 | 1 | | 4 | | | 7 | 7 | |
| | | | | | | | | | 1 | 2 | | 6 | 2 | 5 | 9 | 9 | 5 | | | 2 | | | 4 | 5 | |
| 8 | 2 | | 5 | 2 | 2 | | | | 5 | 4 | 3 | 8 | 6 | 7 | 8 | 6 | 6 | 3 | | 8 | 3 | 1 | 6 | * | 2 |
| | | | | | | | | | 1 | 4 | 2 | 7 | 4 | 6 | 7 | 5 | 5 | 2 | | 8 | 2 | | 5 | * | |
| 9 | | | | | | | 2 | | 5 | 4 | 1 | 6 | 4 | 4 | 7 | 8 | 4 | | | 5 | | | 3 | 3 | |
| | | | | | | | | | 1 | 3 | 1 | 4 | 2 | 4 | 7 | 7 | 3 | | | 4 | - | | 3 | 3 | |
| 10 | 3 | 2 | 3 | 2 | | 3 | 2 | | 5 | 3 | 1 | 7 | 3 | 5 | 9 | 9 | 5 | | | 5 | 1 | 1 | 7 | 7 | |
| | | | | | | | | | 1 | 3 | 1 | 6 | 2 | 3 | 9 | 9 | 4 | | | 5 | | | 5 | 5 | |
| 11 | 2 | 1 | 1 | 1 | 1 | 2 | | 1 | 5 | 4 | 2 | 8 | 5 | 6 | 9 | 9 | 5 | 1 | | 6 | 2 | 2 | 7 | 7 | 4 |
| | | | | | | | | | 1 | 3 | 1 | 8 | 4 | 6 | 9 | 9 | 4 | | | 6 | 1 | 1 | 6 | 5 | 1 |
| 12 | 4 | 2 | 4 | 3 | 2 | 4 | 4 | | 5 | 4 | 3 | 6 | 5 | 7 | 9 | 9 | 8 | 2 | 1 | 5 | * | * | 7 | 6 | 2 |
| | | | | | | | | | 1 | 3 | 2 | 5 | 3 | 6 | 9 | 9 | 7 | | | 4 | 4 | 2 | 7 | 6 | |
| 13 | | | | | | | | | 5 | 4 | 1 | 8 | 3 | 5 | 8 | 8 | 6 | | | 6 | | | 5 | 5 | |
| | | | | | | | | | 1 | 3 | | 4 | 2 | 5 | 8 | 7 | 6 | | | 6 | | | 4 | 5 | |
| 14 | 3 | 2 | 4 | 1 | 2 | 2 | 2 | | 5 | 3 | 2 | 8 | 6 | 5 | 8 | 9 | 4 | 3 | 1 | 7 | 5 | 3 | 8 | 8 | |
| | | | | | | | | | 1 | 2 | 1 | 7 | 4 | 5 | 8 | 9 | 4 | 1 | 1 | 7 | 4 | 3 | 8 | 7 | |
| 15 | 3 | | 4 | 5 | 2 | 5 | 2 | 2 | 5 | 4 | 1 | 8 | 4 | 6 | 9 | 9 | 7 | | | 6 | 4 | 2 | 8 | 7 | |
| | | | | | | | | | 1 | 4 | 1 | 8 | 4 | 6 | 9 | 9 | 7 | | | 6 | 3 | | 6 | 6 | |
| 16 | 1 | | | | 2 | 3 | 2 | 2 | 5 | 3 | | 6 | 3 | 5 | 9 | 8 | 5 | 1 | | 4 | 1 | 2 | 4 | 3 | |
| | | | | | | | | | 1 | 2 | | 4 | 2 | 4 | 9 | 8 | 3 | | | 3 | | | 3 | 1 | |
| 17 | | | | | | 2 | 2 | | 5 | 3 | | 3 | 3 | 3 | * | * | * | | | | | | | | |
| | | | | | | | | | 1 | 1 | | 2 | 1 | 3 | 4 | 5 | 4 | | | | | | | | |
| 18 | | | | 1 | 2 | 5 | 1 | 2 | 5 | 4 | 1 | 7 | 3 | 6 | 8 | 8 | 4 | | | 1 | | | 3 | | |
| | | | | | | | | | 1 | 2 | | 5 | 3 | 5 | 8 | 8 | 3 | | | | | | 1 | | |
| 19 | 3 | 1 | 4 | 3 | 1 | 2 | 2 | | 5 | 3 | 2 | 7 | 3 | 6 | 9 | 9 | 6 | | | 4 | 1 | | 4 | 2 | |
| | | | | | | | | | 1 | 2 | 1 | 6 | 2 | 5 | 9 | 8 | 4 | | | 3 | 1 | | 3 | 1 | |
| 20 | 1 | | | 3 | | | 1 | | 5 | 3 | | 6 | 3 | 5 | 8 | 8 | 5 | | | 3 | | | 3 | 3 | |
| | | | | | | | | | 1 | 2 | | 2 | 1 | 3 | 8 | 5 | 3 | | | 1 | | | 2 | 1 | |
| 21 | 1 | | 1 | | | 1 | 1 | | 5 | 3 | | 6 | 3 | 5 | 8 | 6 | 4 | | | 4 | | | 4 | 2 | |
| | | | | | | | | | 1 | 2 | | 4 | 2 | 4 | 8 | 6 | 4 | | | 2 | | | 2 | 1 | |
| 22 | | | 1 | 1 | | 2 | | 1 | 5 | 4 | 1 | 6 | 3 | 4 | 8 | 8 | 5 | | | | | | 2 | | |
| | | | | | | | | | 1 | 3 | | 4 | 2 | 3 | 7 | 8 | 4 | | | | | | 1 | | |
| 23 | 4 | 3 | 6 | 4 | 2 | 3 | 2 | | 5 | 5 | 4 | 8 | 7 | 6 | 9 | 9 | 6 | 4 | 3 | 8 | 6 | 3 | 9 | 9 | |
| | | | | | | | | | 1 | 4 | 4 | 8 | 6 | 6 | 9 | 9 | 6 | 2 | 1 | 8 | 5 | 3 | 9 | 9 | |
| 24 | 1 | * | 3 | | 1 | 1 | | | 5 | 2 | | * | 1 | * | 8 | 8 | * | | | 3 | | | 4 | 2 | |
| | | | | | | | | | 1 | 1 | | 5 | 1 | 4 | 8 | 8 | 4 | | | 2 | | | 3 | 1 | |
| 25 | | | | | | 2 | 2 | | 5 | 5 | 2 | 6 | 4 | 6 | 9 | 9 | 6 | 1 | | 5 | 3 | 2 | 5 | 6 | |
| | | | | | | | | | 1 | 4 | 1 | 5 | 3 | 6 | 8 | 8 | 6 | | | 4 | 3 | 1 | 5 | 5 | |
| 26 | | | | | | | | | 5 | 1 | | 2 | | | 3 | 3 | 1 | | | 4 | | | 2 | | |
| | | | | | | | | | 1 | | | | | | 2 | 1 | | | | 2 | | | 1 | | |
| 27 | | | | | | | | | 5 | 2 | | 4 | 2 | 4 | 8 | 7 | 4 | | | 4 | 2 | | 3 | 5 | |
| | | | | | | | | | 1 | 2 | | 3 | 2 | 4 | 7 | 5 | 3 | | | 1 | 1 | | 2 | 4 | |

TABLE II-continued

| Compound of Ex. No. | Soil drench 10/kg/ha | | | | | | | Dosage kg/ha | Foliar spray | | | | | | | Pre-emergence | | | | | | | |
|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 28 | | | | | | | | | 5 | 4 | | 6 | 3 | 4 | 8 | 6 | 4 | 2 | 1 | 1 | 2 | | | 4 | 5 |
| | | | | | | | | | 1 | 2 | | 1 | 2 | 2 | 5 | 5 | 3 | 1 | | | 1 | | | 2 | |
| 29 | | | 2 | 2 | 1 | 2 | 2 | 1 | 5 | 4 | | 8 | 4 | 6 | 9 | 9 | 5 | | | 2 | 1 | | | 4 | 3 | 2 |
| | | | | | | | | | 1 | 2 | | 4 | 2 | 6 | 9 | 7 | 4 | | | | | | | 3 | 1 |
| 30 | 1 | | 3 | | 1 | 3 | 1 | | 5 | 6 | 1 | 7 | 4 | 4 | 8 | 8 | 5 | | | 4 | 1 | 1 | | 7 | 4 |
| | | | | | | | | | 1 | 3 | 1 | 5 | 3 | 3 | 8 | 8 | 4 | | | 1 | | | | 4 | 2 |
| 31 | | | 4 | 3 | 1 | 4 | 4 | | 5 | 5 | 3 | 7 | 6 | 5 | 8 | 9 | 7 | 2 | | 7 | 3 | 3 | | 8 | 8 | 2 |
| | | | | | | | | | 1 | 3 | 1 | 6 | 3 | 4 | 8 | 9 | 7 | | | 6 | 2 | 2 | | 8 | 5 | 1 |
| 32 | 1 | 1 | 3 | 4 | 2 | 3 | 2 | 2 | 5 | 3 | 2 | 8 | 4 | 5 | 9 | 9 | 6 | 1 | | 6 | 2 | 2 | | 8 | 7 |
| | | | | | | | | | 1 | 2 | 1 | 5 | 3 | 4 | 9 | 9 | 5 | | | 5 | 2 | 1 | | 7 | 5 |
| 33 | | | 1 | 3 | 1 | 2 | 2 | | 5 | 4 | 1 | 7 | 4 | 5 | 9 | 9 | 6 | | | 4 | | | 1 | 6 | 6 |
| | | | | | | | | | 1 | 4 | | 7 | 3 | 5 | 9 | 9 | 5 | | | 3 | | | 1 | 6 | 5 |
| 34 | | | 3 | 5 | 1 | 2 | 2 | 1 | 5 | 4 | | 8 | 4 | 5 | 9 | 9 | 5 | | | 4 | 1 | 3 | | 6 | 7 |
| | | | | | | | | | 1 | 2 | | 7 | 3 | 5 | 9 | 9 | 5 | | | 3 | | 1 | | 6 | 6 |
| 35 | 2 | 2 | 3 | 5 | 2 | 4 | 2 | | 5 | 4 | 2 | 8 | 6 | 5 | 9 | 9 | 4 | 4 | 2 | 7 | 5 | 3 | | 7 | 8 |
| | | | | | | | | | 1 | 3 | 1 | 7 | 4 | 4 | 9 | 9 | 4 | 2 | 2 | 7 | 5 | 2 | | 7 | 7 |
| 36 | 3 | 4 | 5 | 6 | | 3 | 4 | | 5 | 5 | 4 | 8 | 7 | 7 | 9 | 9 | 7 | 1 | 1 | 5 | 4 | 3 | | 5 | 6 |
| | | | | | | | | | 1 | 4 | 2 | 7 | 6 | 7 | 9 | 9 | 7 | 1 | | 4 | 1 | 1 | | 5 | 5 |
| 37 | 2 | | 3 | 2 | 2 | 3 | 2 | | 5 | 6 | 5 | 8 | 6 | 6 | 8 | 8 | 7 | 2 | | 8 | 3 | | | 8 | 6 |
| | | | | | | | | | 1 | 5 | 1 | 7 | 4 | 5 | 8 | 8 | 7 | | | 4 | 1 | | | 6 | 4 |
| 38 | | | | | | | | | 5 | 1 | | 1 | 2 | * | * | * | * | | | | | | | | |
| | | | | | | | | | 1 | 1 | | 1 | 1 | 2 | 4 | 2 | 2 | | | | | | | | |
| 39 | 3 | 2 | 4 | 4 | 1 | 2 | 2 | | 5 | 6 | 4 | 8 | 6 | 7 | 9 | 9 | 8 | * | * | * | * | * | * | * | * |
| | | | | | | | | | 1 | 5 | 3 | 8 | 5 | 7 | 9 | 9 | 8 | 2 | | 6 | | | | 3 | 2 |
| 40 | | | | | 1 | 2 | 2 | | 5 | 5 | 1 | 6 | 4 | 2 | 8 | 6 | 3 | | | | | | | | |
| | | | | | | | | | 1 | 4 | 1 | * | * | * | * | * | * | | | | | | | | |
| 41 | | | | | 1 | 3 | | | 5 | 4 | 3 | 4 | 4 | 6 | 9 | 7 | 4 | | | | | | | 6 | 4 |
| | | | | | | | | | 1 | 3 | 2 | 2 | 2 | 4 | 9 | 6 | 3 | | | | | | | 4 | 2 |

We claim:

1. A compound of the formula

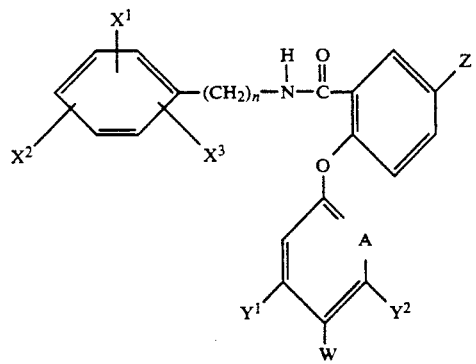

(I)

wherein $X^1$, $X^2$ and $X^3$ each independently represents a hydrogen or halogen atom or an alkyl group; Z represents a hydrogen or halogen atom, or an amino, alkyl, haloalkyl, alkylthio or alkoxy group or a phenoxy group optionally substituted by haloalkyl; $Y^1$ and $Y^2$ each independently represents a hydrogen or halogen atom, or an alkyl, haloalkyl, alkoxy or haloalkoxy; and W represents a hydrogen atom or, when at least one of $Y^1$ and $Y^2$ is other than a hydrogen atom, W represents a hydrogen or halogen atom.

2. A compound according to claim 1, wherein $X^1$, $X^2$ and $X^3$ each independently represents a hydrogen or halogen atom or a $C_1$-$C_4$ alkyl group.

3. A compound according to claim 1, wherein Z represents a hydrogen or halogen atom, or an amino, $C_1$-$C_4$ alkyl, $C_1$-$C_4$ haloalkyl, $C_1$-$C_4$ alkylthio or $C_1$-$C_4$ alkoxy group or a phenoxy group optionally substituted by $C_1$-$C_4$ haloalkyl.

4. A compound according to claim 1, wherein $Y^1$ and $Y^2$ each independently represents a hydrogen or halogen atom, or a $C_1$-$C_4$ alkyl, $C_1$-$C_4$ haloalkyl, $C_1$-$C_4$ alkoxy or $C_1$-$C_4$ haloalkoxy group.

5. A herbicidal composition which comprises a carrier and, as active ingredient a compound of formula I as claimed in claim 1.

6. A composition according to claim 5, which comprises at least two carriers, at least one of which is a surface-active agent.

7. A method of combating undesired plant growth at a locus, which comprises treating the locus with an effective amount of a compound of formula I as claimed in claim 1.

8. A method of combating undesired plant growth at a locus, which comprises treating the locus with an effective amount of a composition of claim 5.

* * * * *

UNITED STATES PATENT AND TRADEMARK OFFICE
CERTIFICATE OF CORRECTION

PATENT NO.   : 5,304,532
DATED        : April 19, 1994
INVENTOR(S)  : David Munro, et. al.

It is certified that error appears in the above-indentified patent and that said Letters Patent is hereby corrected as shown below:

Title page, item [57], Abstract, 8 lines from the bottom, "$ZY^2$" should read -- $Y^2$ --.

Column 17, Claim 1, the formula should be as follows:

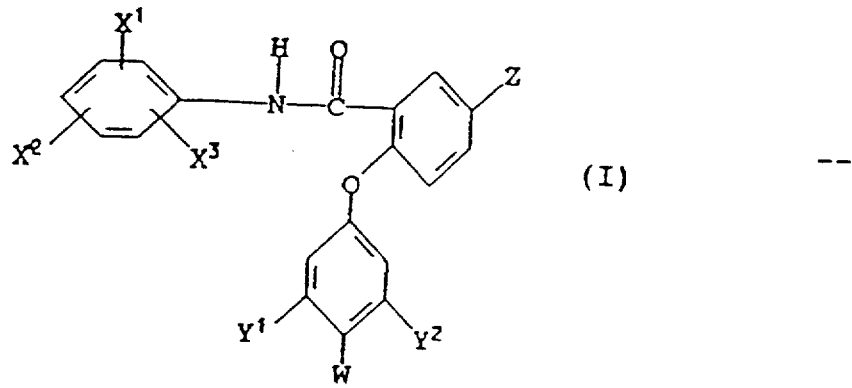

(I)

Signed and Sealed this

Ninth Day of August, 1994

Attest:

BRUCE LEHMAN

Attesting Officer          Commissioner of Patents and Trademarks